(12) United States Patent
Lee

(10) Patent No.: US 7,410,657 B2
(45) Date of Patent: Aug. 12, 2008

(54) ALTERNATIVE REMEDY-BASED COMPOSITION FOR ENHANCING FERTILITY

(76) Inventor: Ai Ja Lee, 300 Winston Dr., Apt. No. 1723, Cliffside Park, NJ (US) 07010

( * ) Notice: Subject to any disclaimer, the term of this patent is extended or adjusted under 35 U.S.C. 154(b) by 0 days.

(21) Appl. No.: 10/955,871

(22) Filed: Sep. 30, 2004

(65) Prior Publication Data

US 2006/0068033 A1 Mar. 30, 2006

(51) Int. Cl.
*A61K 36/254* (2006.01)
*A61K 36/906* (2006.01)
*A61K 36/48* (2006.01)
*A01N 65/10* (2006.01)

(52) U.S. Cl. .............. 424/725; 424/728; 424/756; 424/757

(58) Field of Classification Search .............. 424/725
See application file for complete search history.

(56) References Cited

U.S. PATENT DOCUMENTS

| | | | |
|---|---|---|---|
| 4,006,227 A | 2/1977 | Gallegos et al. | |
| 4,689,230 A | 8/1987 | Ayoub | |
| 5,736,144 A | 4/1998 | Gideon | |
| 6,291,533 B1 | 9/2001 | Fleischner | |
| 6,352,713 B1 * | 3/2002 | Kirschner et al. | 424/441 |
| 6,497,885 B2 | 12/2002 | Trant | |
| 6,503,529 B1 | 1/2003 | Fleischner | |
| 6,610,331 B1 | 8/2003 | Sweazy et al. | |
| 2002/0031559 A1 * | 3/2002 | Liang et al. | 424/725 |
| 2003/0108629 A1 * | 6/2003 | Chou | 424/765 |
| 2003/0195178 A1 * | 10/2003 | Li | 514/171 |
| 2004/0071796 A1 * | 4/2004 | Li | 424/735 |
| 2004/0105902 A1 * | 6/2004 | Chen | 424/756 |
| 2004/0109904 A1 * | 6/2004 | Li | 424/725 |
| 2004/0185121 A1 * | 9/2004 | Yu | 424/725 |
| 2004/0265397 A1 * | 12/2004 | Wang et al. | 424/725 |

FOREIGN PATENT DOCUMENTS

| | | | |
|---|---|---|---|
| CN | 1066603 | * | 12/1992 |
| CN | 1154251 | * | 7/1997 |
| KR | 2003005129 | * | 1/2003 |

OTHER PUBLICATIONS

Duke, J.A. "The Green Pharmacy," Rodale Press, 1997, pp. 338-342.*
Wing, YK; HKMJ, vol. 7; No. 4; Dec. 2001; p. 392-402. (11 pages total).*
"Atractylodes macrocephala: Plants for a Future" (4 pages total).*
Wing, YK; HKMJ, vol. 7; No. 4; Dec. 2001; p. 392-402. (11 pages total).*
Registered Charity No. 1057719, Plants for a Future, Atractylodes macrocephala, [online] URL <http://www.pfaf.org/database/plants.php?Atractylodes+macrocephala>, accessed Dec. 28, 2006, pp. 1-4.*

* cited by examiner

*Primary Examiner*—Patricia Leith
*Assistant Examiner*—Qiuwen Mi

(57) ABSTRACT

A plurality of herbs is combined to produce a composition that enhances and promotes fertility in females. One herbal composition comprises 40 herbs, the so-called "A" formula, and another herbal composition comprises 40 herbs, the so-called "B" formula. Some herbs are present in both formulas. The second formula is administered after the first formula only if conception occurs.

3 Claims, No Drawings

ALTERNATIVE REMEDY-BASED COMPOSITION FOR ENHANCING FERTILITY

BACKGROUND OF THE INVENTION

The present invention is related to fertility-enhancing compositions. More specifically, the present invention is related to an alternative remedy-based, natural composition for improving natural fertility process.

It is estimated that 1 in 6 couples experience difficulties in conceiving a child. Some of the difficulties may be linked to infertility in a woman caused by a medical condition, for example. Other difficulties, however, are not related to infertility and may be attributed to everyday stress, unhealthy diets, use of tobacco or alcohol, etc. In this case, what seems like interminable delay in getting pregnant may cause additional stress and frustration, exacerbating the situation and spiraling further into a proverbial vicious circle.

While prescription or over-the-counter drugs may be efficacious in addressing the fertility problems, alternative medicine based on herbs and other natural ingredients appears to be more preferable from the overall health viewpoint. Once considered remedies mostly used by New Age hippies, herbal compositions are now part of a health regimen by two out of five Americans and has become mainstream.

A need therefore exists for an alternative medicine-based, natural solution to the above difficulties experienced by a woman trying to conceive a child.

SUMMARY OF THE INVENTION

It is an object of the present invention to provide an herb-based composition for enhancing fertility.

The above and other objects are achieved by an alternative remedy-based composition. According to one embodiment of the present invention, an alternative remedy-based composition comprises a first formula consisting of a first plurality of herbs and a second formula consisting of a second plurality of herbs. Some individual herbs are present in the first and second formulas. The second formula is administered after the first formula only if conception occurs such that the combination of the first and second formulas enhances fertility in females.

DETAILED DESCRIPTION OF PREFERRED EMBODIMENTS

In accordance with one embodiment of the present invention, a number of herbs are combined to produce a composition that enhances and promotes fertility in females. According to this embodiment, one herbal composition comprises 40 herbs, the so-called "A" formula. Further according to this embodiment of the present invention, another herbal composition comprises 40 herbs, the so-called "B" formula. Some herbs are present in both formulas.

"A" formula is typically administered for 2 months for conception to occur. After conception, "B" formula is administered for 1 month to prevent miscarriage. If, however, conception does not occur after 2 months, "A" formula is continued for one more month. Using the inventive composition, typical conception takes place within 3 months from the beginning of the course. Other factors, such as stress, alcohol, etc., may lengthen the conception period by additional 1 or 2 months.

Each herbal ingredient in the "A" and "B" formulas is approximately between 3 and 10 grams in dry weight. To be more effective, the exact weight for each herbal ingredient depends on the female's weight. For an average female, each herbal ingredient is approximately 4 grams in weight.

According to one embodiment of the present invention, for an average female each "A" and "B" formula weighs approximately 164 grams, comprising the below-mentioned herbal ingredients. Such "raw" herbal combination in each formula is boiled in hot water to produce approximately 18 ounces of liquid. The resulting liquid is a daily dosage: it is administered 3 times a daily, 6 ounces at a time, at a lukewarm temperature.

It will be appreciated that both formulas are administered orally in the preferred embodiment of the present invention. According to additional embodiments of the present invention, each formula may be administered in capsules, pills, caplets, tablets, and the like forms, as known to those skilled in the art.

The "A" formula comprises the following herbs listed in no particular order according to their pharmaceutical names:
1) Radix Polygalae Tenuifoliae
2) Semen Ziziphi Spinosae
3) Radix Ginseng
4) Rhizoma Atractylodis Macrocephalae
5) Rhizoma Zingiberis Officinalis Recens
6) Sclerotium Poriae Cocos
7) Radix Astragali
8) Radix Ligustici Wallichii
9) Radix Angelicae Sinensis
10) Radix Rehmanniae Glutinosae Conquitae
11) Radix Paeoniae Rubra
12) Radix Bupleuri
13) Ramulus Cinnamomi Cassiae
14) Arillus Euphoriae Longanae
15) Radix Saussureae Seu Vladimiriae
16) Fructus Lycii Chinensis
17) Fructus Schisandrae Chinensis
18) Fructus Rubi
19) Semen Cnidii Monnieri
20) Semen Cuscutae
21) Semen Persicae
22) Flos Carthami Tinctorii
23) Folium Artemisiae
24) Herba Agastaches Seu Pogostemi
25) Folium Perillae Frutescentis
26) Herba Leonuri Heterophylli
27) Rhizoma Cyperi Rotundi
28) Radix Glycyrrhizae Uralensis
28) Fructus Ziziphi Jujubae
30) Fructus Foeniculi Vulgaris
31) Fructus Evodiae Rutaecarpae
32) Semen Plantaginis
33) Radix Ledebouriellae Sesloidis
34) Radix Scutellariae Baicalensis
35) Tuber Asparagi Cochinchinensis
36) Massa Fermentata
37) Fructus Hordei Vulgaris Germinantus
38) Rhizoma Sparganii
39) Rhizoma Curcumae Zedoariae
40) Cornu Cervi Parvum The "B" formula comprises the following herbs listed in no particular order according to their pharmaceutical names:
1) Radix Polygalae Tenuifoliae
2) Semen Ziziphi Spinosae
3) Radix Ginseng
4) Rhizoma Atractylodis Macrocephalae
5) Rhizoma Zingiberis Officinalis Recens
6) Sclerotium Poriae Cocos 7) Radix Astragali
8) Radix Ligustici Wallichii
9) Radix Angelicae Sinensis
10) Radix Rehmanniae Glutinosae Conquitae
11) Radix Paeoniae Lactiflorae
12) Radix Bupleuri
13) Cortex Moutan Radicis
14) Arillus Euphoriae Longanae
15) Radix Saussureae Seu Vladimiriae
16) Fructus Lycii Chinensis
17) Fructus Schisandrae Chinensis
18) Fructus Rubi
19) Semen Cnidii Monnieri
20) Semen Cuscutae
21) Cortex Eucommiae Ulmoidis
22) Gelatinum Asini
23) Folium Artemisiae
24) Herba Leonuri Heterophylli
25) Folium Perillae Frutescentis
26) Herba Agastaches Seu Pogostemi
27) Rhizoma Cyperi Rotundi
28) Fructus Foeniculi Vulgaris
29) Fructus Evodiae Rutaecarpae
30) Radix Glycyrrhizae Uralensis
31) Fructus Ziziphi Jujubae
32) Semen Plantaginis
33) Os Draconis
34) Concha Ostreae
35) Radix Scutellariae Baicalensis
36) Pericarpium Citri Reticulatae
37) Ramus Loranthu Seu Visci
38) Cornu Cervi Parvum
39) Rhizoma Atractylodis
40) Fructus Seu Semen Amomi While the invention has been described and illustrated in connection with preferred embodiments, many variations and modifications may be made without departing from the spirit and scope of the invention, and the invention is thus not to be limited to the precise details of methodology or construction set forth above as such variations and modification are intended to be included within the scope of the invention.

What is claimed is:

1. A composition for enhancing fertility, comprising:
a formula of approximately 4 grams of each of the following: Radix Polygalae Tenuifoliae, Semen Ziziphi Spinosae, Radix Ginseng, Rhizoma Atractylodis Macrocephalae, Rhizoma Zingiberis Officinalis Recens, Sclerotium Poriae Cocos, Radix Astragali, Radix Ligustici Wallichii, Radix Angelicae Sinensis, Radix Rehmanniae Glutinosae Conquitae, Radix Paeoniae Rubra, Radix Bupleuri, Ramulus Cinnamomi Cassiae, Arillus Euphoriae, Longanae, Radix Saussureae Seu Vladimiriae, Fructus Lycii Chinensis, Fructus Schisandrae Chinensis, Fructus Rubi, Semen Cnidii Monnieri, Semen Cuscutae, Semen Persicae, Flos Carthami Tinctorii, Folium Artemisiae, Herba Agastaches Seu Pogostemi, Folium Perillae Frutescentis, Herba Leonuri Heterophylli, Rhizoma Cyperi Rotundi, Radix Glycyrrhizae Uralensis, Fructus Ziziphi Jujubae, Fructus Foeniculi Vulgaris, Fructus Evodiae Rutaecarpae, Semen Plantaginis, Radix Ledebouriellae Sesloidis, Radix Scutellariae Baicalensis, Tuber Asparagi Cochinchinensis, Massa Fermentata, Fructus Hordei Vulgaris Germinantus, Rhizoma Sparganii, Rhizoma Curcumae Zedoariae, and Cornu Cervi Parvum.

2. A composition for enhancing fertility, comprising:
a formula of approximately 4 grams of each of the following: Radix Polygalae Tenuifoliae, Semen Ziziphi Spinosae, Radix Ginseng, Rhizoma Atractylodis Macrocephalae, Rhizoma Zingiberis Officinalis Recens, Sclerotium Poriae Cocos, Radix Astragali, Radix Ligustici Wallichii, Radix Angelicae Sinensis, Radix Rehmanniae Glutinosae Conquitae, Radix Paeoniae Lactiflorae, Cortex Moutan Radicis, Arillus Euphoriae Longanae, Radix Saussureae Seu Vladimiriae, Fructus Lycii Chinensis, Fructus Schisandrae Chinensis, Fructus Rubi, Semen Cnidii Monnieri, Semen Cuscutae, Cortex Eucommiae Ulmoidis, Gelatinum Asini, Folium Artemisiae, Herba Leonuri Heterophylli, Folium Perillae Frutescentis, Herba Agastaches Seu Pogostemi, Rhizoma Cyperi Rotundi, Fructus Foeniculi Vulgaris, Fructus Evodiae Rutaecarpae, Radix Glycyrrhizae Uralensis, Fructus Ziziphi Jujubae, Semen Plantaginis, Os Draconis, Concha Ostreae, Pericarpium Citri Reticulatae, Ramus Loranthu Seu Visci, Cornu Cervi Parvum, Rhizoma Atractylodis, and Fructus Seu Semen Amomi.

3. A method for preparing two formulas to enhance fertility, comprising the steps of:
preparing a first formula by mixing between approximately 3 grams and approximately 10 grams of each of the following components: Radix Polygalae Tenuifoliae, Semen Ziziphi Spinosae, Radix Ginseng, Rhizoma Atractylodis Macrocephalae, Rhizoma Zingiberis Officinalis Recens, Sclerotium Poriae Cocos, Radix Astragali, Radix Ligustici Wallichii, Radix Angelicae Sinensis, Radix Rehmanniae Glutinosae Conquitae, Radix Paeoniae Rubra, Radix Bupleuri, Ramulus Cinnamomi Cassiae, Arillus Euphoriae Longanae, Radix Saussureae Seu Vladimiriae, Fructus Lycii Chinensis, Fructus Schisandrae Chinensis, Fructus Rubi, Semen Cnidii Monnieri, Semen Cuscutae, Semen Persicae, Flos Carthami Tinctorii, Folium Artemisiae, Herba Agastaches Seu Pogostemi, Folium Perillae Frutescentis, Herba Leonuri Heterophylli, Rhizoma Cyperi Rotundi, Radix Glycyrrhizae Uralensis, Fructus Ziziphi Jujubae, Fructus Foeniculi Vulgaris, Fructus Evodiae Rutaecarpae, Semen Plantaginis, Radix Ledebouriellae Sesloidis, Radix Scutellariae Baicalensis, Tuber Asparagi Cochinchinensis, Masa Fermentata, Fructus Hordei Vulgaris Germinantus, Rhizoma Sparganii, Rhizoma Curcumae Zedoariae, and Cornu Cervi Parvum;
reducing the first formula to a liquid state by adding water and heating the mixture;
preparing a second formula by mixing between approximately 3 and approximately 10 grams of each of the following components: Radix Polygalae Tenuifolaie, Semen Ziziphi Spinosae. Radix Ginseng, Rhizoma Atractylodis Macrocephalae, Rhizoma Zingiberis Officinalis Recens, Sclerotium Poriae Cocos, Radix Astragali, Radix Ligustici Wallichii, Radix Angelicae Sinensis, Radix Rehmanniae Glutinosae Conquitae, Radix Paeoniae Lactiflorae, Radix Bupleuri, Cortex Moutan Radicis, Arillus Euphoriae Longanae, Radix Saussureae Seu Vladimiriae, Fructus Schisandrae Chinensis, Fructus Rubi, Semen Cnidii Monnieri, Semen Cuscutae, Cortex Eucommiae Ulmoidis, Gelatinum Asini, Folium Artemisiae, Herba Leonuri Heterophylii, Folium Perillae Frutescentis, Herba Agastaches Seu Pogostemi, Rhizoma Cyperi Rotundi, Fructus Foeniculi Vulargis, Fructus Evodiae Rutaecarpae, Radix Glycyrrhizae Uralensis, Fructus Ziziphi Jujubae, Semen Plantaginis, Os Draconis, Concha Ostreae, Radix Scutellariae Baicalensis, Pericarpium Citri Reticulatae, Ramus Loranthu Seu Visci, Cornu Cervi Parvum, Rhizoma Atractylodis, and Fructus Seu Semen Amomi; and reducing the second formula to a liquid state by adding water and heating the mixture.

* * * * *